US009126930B2

(12) United States Patent
Doerwald

(10) Patent No.: US 9,126,930 B2
(45) Date of Patent: Sep. 8, 2015

(54) METHOD FOR PREPARATION OF OCTAHYDROCYCLOPENTA[C]PYRROLE

(71) Applicant: Lonza Ltd, Visp (CH)

(72) Inventor: Florencio Zaragoza Doerwald, Visp (CH)

(73) Assignee: Lonza Ltd., Visp (CH)

( * ) Notice: Subject to any disclaimer, the term of this patent is extended or adjusted under 35 U.S.C. 154(b) by 0 days.

(21) Appl. No.: 14/414,371

(22) PCT Filed: Jan. 3, 2013

(86) PCT No.: PCT/EP2013/050029
§ 371 (c)(1),
(2) Date: Jan. 12, 2015

(87) PCT Pub. No.: WO2013/102634
PCT Pub. Date: Jul. 11, 2013

(65) Prior Publication Data
US 2015/0183740 A1    Jul. 2, 2015

Related U.S. Application Data

(60) Provisional application No. 61/583,703, filed on Jan. 6, 2012, provisional application No. 61/672,534, filed on Jul. 17, 2012.

(30) Foreign Application Priority Data

| Jan. 6, 2012 | (EP) | 12150350 |
|---|---|---|
| Jan. 30, 2012 | (EP) | 12153038 |
| May 14, 2012 | (EP) | 12167873 |
| Jul. 17, 2012 | (EP) | 12176777 |
| Oct. 12, 2012 | (EP) | 12188373 |

(51) Int. Cl.
*C07D 209/52* (2006.01)

(52) U.S. Cl.
CPC .................... *C07D 209/52* (2013.01)

(58) Field of Classification Search
None
See application file for complete search history.

(56) References Cited

U.S. PATENT DOCUMENTS

| 3,192,262 A | 6/1965 | Schreyer |
| 3,501,495 A | 3/1970 | Beregi et al. |
| 5,244,888 A | 9/1993 | DeBernardis et al. |
| 6,320,058 B2 | 11/2001 | Souvie et al. |
| 2001/0023294 A1 | 9/2001 | Souvie et al. |

FOREIGN PATENT DOCUMENTS

| DE | 1695677 | 6/1972 |
| EP | 1127876 | 8/2001 |
| JP | H05-070429 | 3/1993 |
| JP | 2001261643 | 9/2001 |
| WO | WO 95/06631 | 3/1995 |
| WO | WO 2009/140279 | 11/2009 |
| WO | WO 2010/069566 | 6/2010 |

OTHER PUBLICATIONS

European Search Report for EP12150350, completed Jul. 4, 2012.
European Search Report for EP12176777, completed Dec. 3, 2012.
International Preliminary Report on Patentability for PCT/EP2013/050029, completed Dec. 9, 2013.
International Search Report for PCT/EP2013/050029, completed Apr. 26, 2013.
Cariou, Michel et al., "Synthéses ápartir de la cyano-2-cyclopentaone. Préparation du dicyano-1,2 cyclopenténe," C. R. Acad. Sc. Paris, t. 278, pp. 1457-1460 (1974).
Fleming, Fraser F. et al., "Metalated Nitriles: Chelation-Controlled Cyclizations to cis and trans Hydrindanes and Decalins," J. Org. Chem., vol. 72, No. 4, pp. 1431-1436 (2007).
Fleming, Fraser F. et al., Supporting Information for "Metalated Nitriles: Chelation-Controlled Cyclizations to cis and trans Hydrindanes and Decalins," J. Org. Chem., vol. 72, No. 4. pp. S1-S91 (2007).
Griot, R. von, "Über einige Azabicyclo-octane und deren Derivate," Helvetica Chmica Acta, Verlag Helvetica, Chmica Acta, vol. 42, No. 1, pp. 67-72 (1959).
Meyer, Michael D. et al., Structure-Activity Studies for a Novel Series of Tricyclic Substituted Hexahydrobenz[e]isoindole $\alpha_{1A}$ Adrenoceptor Antagonists as Potential Agents for the Symptomatic Treatment of Benign Prostatic Hyperplasia (BPH), Journal of Medicinal Chemistry, vol. 43, No. 8, pp. 1586-1603 (2000).
Müller, E., "Methoden der organischem Chemie," George Thieme Verlag, pp. 353-360 (1957).
Najer, Henry et al., Guanidines douées d'activitéantihypertensive, $3^{fr}$ mémoire: N-β-guanidinoéthyl azabicyclo alcanes, Bulletin De La Societe Chimique De France, Societe Francaise De Chirnie, pp. 1593-1597 (1962).
Thompson, Quentin E., "Adiponitrile—A Novel Self-Condensation Sequence," pp. 5483-5487 (1958).

*Primary Examiner* — Michael Barker

(74) *Attorney, Agent, or Firm* — Dority & Manning, P.A.

(57) ABSTRACT

The invention discloses a method for the preparation of octahydrocyclopenta[c]pyrrole, also called 3-azabicyclo[3.3.0]octane, by hydrogenation of 1,2-dicyanocyclo-1-pentene.

6 Claims, No Drawings

METHOD FOR PREPARATION OF OCTAHYDROCYCLOPENTA[C]PYRROLE

RELATED APPLICATIONS

This application is the national stage entry of International Patent Application No. PCT/EP2013/050029 having a filing date of Jan. 3, 2013, which claims the filing benefit of European Patent Application No. 12150350.2 having a filing date of Jan. 6, 2012, U.S. Provisional Application No. 61/583,703 having a filing date of Jan. 6, 2012, European Patent Application No. 12153038.0 having a filing date of Jan. 30, 2012, European Patent Application No. 12167873.4 having a filing date of May 14, 2012, European Patent Application No. 12176777.6 having a filing date of Jul. 17, 2012, U.S. Provisional Application No. 61/672,534 having a filing date of Jul. 17, 2012, and European Patent Application No. 12188373.0 having a filing date of Oct. 12, 2012, all of which are incorporated herein by reference in their entirety.

The invention discloses a method for the preparation of octahydrocyclopenta[c]pyrrole, also called 3-azabicyclo[3.3.0]octane, by hydrogenation of 1,2-dicyanocyclo-1-pentene.

Octahydrocyclopenta[c]pyrrole is an important intermediate for the preparation of various biologically active compounds, such as antidiabetics and antivirals.

WO 2009/140279 A2 discloses the use of compound of formula (I) as an intermediate for the preparation of the antidiabetic sulfonylurea gliclazide, compound of formula (I-gli).

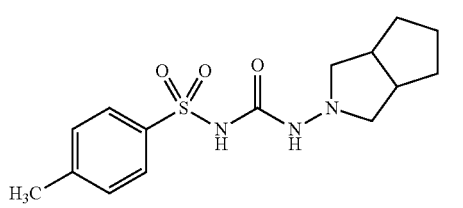
(I-gli)

Moreover, protected derivatives of 3-azabicyclo[3.3.0]octane have been used as intermediates for the preparation of antivirals, such as telaprevir.

Various methods have been reported in the literature for the preparation of compound of formula (I). Most of them are based on a Dieckmann cyclization of diethyl or dimethyl adipate, followed by cyanohydrin formation and reduction of an intermediate cyclic amide or imide, as disclosed for instance in WO 2009/140279 A2. The reduction of amides or imides requires expensive reducing reagents, such as LiAlH$_4$ or borane, which generate large amounts of inorganic salts as waste. Alternatively, the reduction can be achieved in low yield by high-pressure, high-temperature two-step hydrogenation of 2-cyano-1-cyclopentenecarboxylic acid ester with firstly a Raney catalyst and secondly a copper chromite catalyst as disclosed for instance in JP 05-070429 A.

DE 1695677 B discloses, that 3-aza-bicyclo alkane can be prepared in two steps by converting corresponding 1,2-dicarboxylic acids of cyclopropane, cyclobutane or cyclopentane into their imides and subsequent reduction of these imides with lithium aluminum hydride.

EP 1127876 A1 discloses the preparation of 3-aza-bicyclo alkane by hydrogenation of phthalonitrile.

U.S. Pat. No. 3,192,262 B discloses that cis-1,2-dicyanocyclobutane can be converted by hydrogenation into 3-aza(3.2.0)bicycloheptane.

None of the prior art discloses a method starting from unsaturated dicyano cycloalkane, wherein in one step both the reduction of the unsaturated C—C bond and the cyclisation of the two cyano residues is effected.

1,2-Dicyanocyclopentane is not known in literature and would need to be synthesized from the compound of formula (II), as defined below, resulting again in a two step synthesis.

There was a need for a method for the preparation of compound of formula (I) from inexpensive starting materials without the use of expensive hydrides or borane as reducing reagent, or of high-temperature hydrogenations with copper chromite, or of a two step process, such as a two step hydrogenations using two different catalysts or such as a synthesis starting from 1,2-dicyanocyclopentane.

In the text, the following abbreviations mean
DABCO diazabicyclo[2.2.2]octane,
hexanes mixture of isomeric hexanes,
THF tetrahydrofuran,
quant. quantitative,
if not otherwise stated.

Subject of the invention is a method for the preparation of a compound of formula (I);

(I)

the method comprises a reaction (A), wherein a compound of formula (II) is reacted with a reagent (A-rea) in the presence of a catalyst (A-cat),

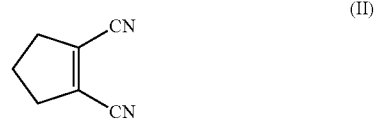
(II)

reagent (Area) is hydrogen;
catalyst (A-cat) is a catalyst conventionally used in hydrogenation reactions of unsaturated organic compounds.

Compound of formula (II) is 1,2-dicyanocyclo-1-pentene.

Reaction (A) is a reduction. The reaction mechanism is not known. The unsaturated compound of formula (II), which is fed into the reactor in the beginning, can be converted during the course of the reaction (A) into one of the other unsaturated compounds of formula (II-c) or (II-d) by isomerization, or can be reduced to the saturated compound of formula (II-a), before the cyclisation takes place during reaction (A). Or at first the cyclisation takes place and then the double bond is reduced. Or the C—C double bond is reduced during one of the intermediate steps or in between two intermediate steps of the cyclisation.

(II-a)

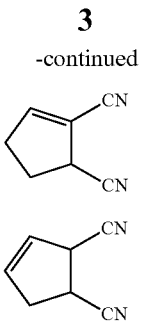

Preferably, the molar amount of reagent (A-rea) is from 6000 equivalents to 6 equivalents, more especially from 600 equivalents to 6 equivalents, even more especially 100 equivalents to 6 equivalents, the equivalents being based on the molar amount of compound of formula (II).

Reaction (A) can be done under pressure, such as from atmospheric pressure to 600 bar.

The amount of reagent (A-rea) used in reaction (A) is in molar excess to compound of formula (II) and can be adjusted by applying and optionally maintaining pressure with reagent (A-rea), said pressure being preferably 600 bar to 10 bar, more preferably 300 bar to 20 bar, even more preferably 200 bar to 50 bar.

Preferably, reaction (A) is done at a temperature (A-temp) of 300° C., to 10° C., more preferably of 200° C. to 50° C., even more preferably of 150° C. to 80° C., especially of 145° C. to 80° C.

Preferably, the reaction time of reaction (A) is from 10 min to 72 h, more preferably from 60 min to 48 h, even more preferably from 5 h to 36 h.

Preferably, catalyst (A-cat) is selected from the group consisting of metalcatalyst (A-metcat), metalcatalyst (A-metcat) on a support (A-sup) and mixtures thereof;

metalcatalyst (A-metcat) is a substance conventionally used in organic reduction reactions and is preferably a substance derived from Pd(0), Pd (I), Pd(II), Ni(0), Ni(I), Ni(II), Pt(0), Pt(I), Pt(II), Pt(IV), Co(0), Co(II), Ru(0), Ir(0), Rh(0), Rh(I), Rh(III), Cr(III), Cu(0), Cu(I) or Cu(II);

support (A-sup) is a support conventionally used for supporting metalcatalysts, which are used in organic reduction reactions.

Preferably, metalcatalyst (A-metcat) is selected from a substance derived from Pd(0), Ni(0), Pt(0), Pt(IV), Co(0), Co(II), Ru(0), Ir(0), Rh(0), Rh(I), Cr(III), Cu(I) or Cu(II), or mixtures thereof;

more preferably, metalcatalyst (A-metcat) is selected from a substance derived from Pd(0), Ni(0), Pt(0), Pt(IV), Ru(0), Rh(0) or Co(0), or mixtures thereof;

even more preferably, metalcatalyst (A-metcat) is selected from a substance derived from Pd(0), Pt(0), Pt(IV), Ru(0) or Rh(0) or mixtures thereof.

Preferably, support (A-sup) is a support conventionally used for supporting metalcatalysts, which are used in heterogeneously catalyzed organic reactions.

More preferably, support (A-sup) is carbon or an inorganic substance conventionally used for supporting metalcatalysts, which are used in heterogeneously catalyzed organic reactions.

Even more preferably, support (A-sup) is selected from the group consisting of carbon, of alumina, of oxides, sulfates and carbonates of metals, said metals are selected from the group consisting of alkaline earth metals, Al, Si, Ce, Zr, La, Ti and Zn, of mixed metal oxides of said metals, of mixed metal carbonates of said metals, of mixed metal oxides carbonates of said metals and of mixtures thereof.

Especially, support (A-sup) is selected from the group consisting of carbon, alumina, alkaline earth oxides, alkaline earth carbonates, silica, zeolithes, oxides, mixed metal oxides and mixed metal carbonates of Ce, Zr, La, Ti and Zn, and mixtures thereof.

More especially, support (A-sup) is carbon or alumina.

Carbon as support comprises any type of carbon, preferably carbon as support is selected from the group consisting of charcoal and graphite.

Preferably, if metalcatalyst (A-metcat) is derived from Pd(0), Pd(I) or Pd(II), then catalyst (A-cat) is selected from the group consisting of
Pd, PdO, PdCl$_2$, Pd(OAc)$_2$, Pd on carbon, on Al$_2$O$_3$, or on BaSO$_4$, and mixtures thereof;
more preferably selected from the group consisting of Pd, PdO, Pd on carbon, on Al$_2$O$_3$, or on BaSO$_4$, and mixtures thereof;
even more preferably selected from the group consisting of Pd, PdO, Pd on carbon, and mixtures thereof;
especially selected from the group consisting of Pd and Pd on carbon.

Preferably, if metalcatalyst (A-metcat) is derived from Ru(0), then catalyst (A-cat) is Ru on a support (A-sup), and support (A-sup) is preferably carbon or alumina.

Preferably, if metalcatalyst (A-metcat) is derived from Ni(0), Ni(I) or Ni(II) then catalyst (A-cat) is Raney-Ni or Ni on a support (A-sup), and support (A-sup) is preferably SiO$_2$.

Preferably, if metalcatalyst (A-metcat) is derived from Cu(0), Cu(I) or Cu(II), then catalyst (A-cat) is selected from the group consisting of Cu, CuCl, copper chromite, and CuCl$_2$.

Preferably, if metalcatalyst (A-metcat) is derived from Co(0) or Co(II), then catalyst (A-cat) is selected from the group consisting of Raney-cobalt, Co(OH)$_2$, and CoO.

Preferably, if metalcatalyst (A-metcat) is derived from Ir(0), then catalyst (A-cat) is selected from the group consisting of Ir, Ir on carbon, Ir on Al$_2$O$_3$, and Ir on calcium carbonate.

Preferably, if metalcatalyst (A-metcat) is derived from Rh(0), Rh(I), or Rh(III), then catalyst (A-cat) is selected from the group consisting of Rh, Rh on carbon, Rh on alumina, Rh on Al$_2$O$_3$, Rh$_2$O$_3$, and RhCl(PPh$_3$)$_3$.

Preferably, if metalcatalyst (A-metcat) is derived from Pt(0), Pt(II), or Pt(IV), then catalyst (A-cat) is selected from the group consisting of Pt, Pt on carbon, Pt on Al$_2$O$_3$, Pt on calcium carbonate, Pt on barium sulfate, Pt on silicon dioxide, PtO$_2$, and PtCl$_2$.

Preferably, if metalcatalyst (A-metcat) is derived from Cr(III), then catalyst (A-cat) is copper chromite.

Preferably, catalyst (A-cat) is selected from the group consisting of copper chromite, Raney nickel, Raney cobalt, platinum on carbon, palladium on carbon, ruthenium on carbon, rhodium on alumina and rhodium on carbon;

more preferably, catalyst (A-cat) is selected from the group consisting of Raney nickel, Raney cobalt, platinum on carbon, palladium on carbon, ruthenium on carbon, rhodium on alumina and rhodium on carbon;

even more preferably, catalyst (A-cat) is selected from the group consisting of platinum on carbon, ruthenium on carbon, rhodium on alumina and rhodium on carbon;

even more preferably, catalyst (A-cat) is platinum on carbon, rhodium on alumina or rhodium on carbon.

When catalyst (A-cat) is platinum on carbon, ruthenium on carbon or rhodium on carbon, then carbon as support is preferably charcoal.

Preferably, the molar amount of metalcatalyst (A-metcat) is from 0.001 to 1000%, more preferably from 0.001 to 100%, even more preferably 0.5 to 30%, the % being based on the molar amount of compound of formula (II).

Preferably, when catalyst (A-cat) comprises a support ort (A-sup), the amount of support (A-sup) is from 20% to 99.99%, more preferably from 40% to 99.9%, even more preferably from 70% to 99.5%, the % being % by weight and are based on the total weight of catalyst (A-cat).

In one embodiment, reaction (A) is done or carried out in the presence of an auxiliary substance (A-aux), auxiliary substance (A-aux) is selected from the group consisting of N(R1)(R2)R3, diazabicyclo[2.2.2]octane, [N(R4)(R5)(R6)R7$^+$][X$^-$], sodium fluoride, potassium fluoride, sodium hydroxide, potassium hydroxide, sodium carbonates, potassium carbonate, sodium hydride, acetic acid, formic acid and hydrogen chloride;

R1, R2 and R3 are identical or different and independently selected from the group consisting of H and $C_{1-4}$ alkyl;

R4, R5, R6 and R7 are identical or different and independently selected from the group consisting of H and $C_{1-4}$ alkyl;

X$^-$ is selected from the group consisting of fluoride, chloride, hydroxide and carbonate.

Preferably, R1, R2 and R3 are identical and selected from the group consisting of H and $C_{1-4}$ alkyl;

more preferably are identical and selected from the group consisting of H, methyl, ethyl and butyl;

even more preferably are identical and are methyl or ethyl.

Preferably, R4, R5, R6 and R7 are identical and selected from the group consisting of H and $C_{1-4}$ alkyl;

more preferably are identical and selected from the group consisting of H, methyl, ethyl and butyl;

even more preferably are identical and are butyl.

Preferably, X$^-$ is fluoride.

In particular, auxiliary substance (A-aux) is selected from the group consisting of ammonia, trimethylamine, triethylamine, diazabicyclo[2.2.2]octane, tetrabutylammonium fluoride, sodium fluoride, potassium fluoride, sodium hydroxide, potassium hydroxide, sodium carbonates, potassium carbonate, sodium hydride, acetic acid, formic acid and hydrogen chloride.

Preferably, the molar amount of auxiliary substance (A-aux) is from 1000 to 1%, more preferably from 500 to 10%, even more preferably 300 to 50%, the % being based on the molar amount of compound of formula (II).

Reaction (A) can be done in gaseous phase. Reaction (A) can be done with gaseous compound of formula (II).

In one embodiment, reaction (A) is done or carried out without a solvent.

In another embodiment, reaction (A) is done or carried out in a solvent (A-sol).

Preferably, solvent (A-sol) is selected from the group consisting of water, acetic acid, propionic acid, tetrahydrofuran, 2-methyl-tetrahydrofuran, dioxane, 1,2-dimethoxyethane, methanol, ethanol, 1-propanol, 2-propanol, butanol, pentanol, ethylene glycol, glycerol and mixtures thereof;

more preferably from the group consisting of acetic acid, tetrahydrofuran, 2-methyl-tetrahydrofuran, methanol, ethanol, 1-propanol and mixtures thereof;

even more preferably solvent (A-sol) is tetrahydrofuran.

Preferably, the amount of solvent (A-sol) is from 0.5 to 200 fold, more preferably from 2 to 100 fold, even more preferably from 5 to 60 fold, of the weight of compound of formula (II).

Preferably, reaction (A) is done with low water content or even in the absence of water. Absence of water means, that water is not used as solvent and solvent (A-sol) is preferably used in dried form; the residual water in solvent (A-sol) is preferably not more than 1% (w/w), more preferably not more than 0.1% (w/w), even more preferably not more than 0.05% (w/w), especially not more than 0.01% (w/w).

Compound of formula (II) is a known compounds and can be prepared by known methods. The cyclization of adiponitrile to 1-cyano-2-amino-1-cyclopentene and the hydrolysis of this product to 2-cyanocyclopentanone have been reported, for instance in Thompson, J. Am. Chem. Soc., 1958, 80, 5483-5487. The conversion of 2-cyanocyclopentanone to 1,2-dicyanocyclo-1-pentene, i.e. compound of formula (II), has also been reported, for instance in Cajon et al., Compt. Rend. Acad. Sci. Paris Serie C, 1974, 278, 1457-1460. Compound of formula (II) can also be prepared from cyclopentanone as disclosed in WO 95/06631 A1.

Reaction (A) can be done under inert atmosphere. The inert atmosphere can be made from a gas (A-gas) selected from the group consisting of nitrogen, helium, neon, argon, carbon dioxide and mixtures thereof.

The method can be conducted batch wise or continuously. In case of a continuous way, i.e. the reaction (A) is done in a continuous way in a reactor for continuous reactions, called continuous reactor in the following. Preferably, a melt or a mixture, preferably a solution, of compound of formula (II) in solvent (A-sol), and reagent (A-rea) are continuously added into the continuous reactor, such as a tube reactor or a micro reactor; compound of formula (II) and reagent (A-rea) can be added as a mixture or separately. The continuous reactor is, preferably precharged with catalyst (A-cat), heated, preferably preheated, to the desired temperature (A-temp), and the product is removed at the other end of the continuous reactor. Preferably, the whole zone of the continuous reactor, where the reaction (A) takes place, and where a possible catalyst (A-cat) is located, is heated to the desired temperature (A-temp). The time of contact of compound of formula (II) with reagent (A-rea) will depend on the concentration of compound of formula (II) and of reagent (A-rea), on the addition rate of compound of formula (II) and reagent (A-rea) into the continuous reactor, on the flow rate (A-flow) of compound of formula (II) and of reagent (A-rea), and optionally on the flow rate of an optional gas (A-gas).

In case of a continuous reaction (A), the process parameters can be adjusted in such a way, that a high conversion of compound of formula (II) into compound of formula (I) is attained, but the amount of byproducts is kept low.

In another embodiment, a continuous reaction (A) can be done in such a way, that only a low, preferably equal or below 40%, conversion rate of compound of formula (II) into compound of formula (I) is attained, the conversion rate in % are weight % of compound of formula (I) based on the weight of compound of formula (II).

Optionally in case of a continuous reaction (A), the crude product mixture comprising compound of formula (I) and compound of formula (II), and reagent (A-rea) can be fed again into the continuous reactor and be subjected again to the conditions of reaction (A). Such a technique would be suitable for a continuous loop reactor set-up.

A continuous method or continuous reaction (A) has the advantage, that residence time of the product, i.e. compound of formula (I), at the elevated temperature (A-temp) and optionally in the solvent (A-sol) can be minimized, thereby side reactions can be avoided or at least minimized.

Compound of formula (II) can inter alia be added to a reactor either as a gas, as a melt or as a mixture with or a solution in solvent (A-sol).

If a mixture of compound of formula (I) and compound of formula (II) is obtained, compound of formula (I) can be separated by conventional separation techniques, such as filtration, distillation or crystallization.

The compound of formula (I) can be isolated, purified, and analyzed using conventional techniques, well known to those skilled in the art. For instance, in the case of a batch reaction, the reaction mixture can be filtered to remove the catalyst, and then distilled. For instance, in the case of a continuous reaction, the gases leaving a reactor can be cooled, and the products of the reaction can be collected in a freezing trap. Alternatively, the gases leaving a reactor can be conveyed into a cold inert solvent, such as solvent (A-sol) or dichloromethane, preferably dichloromethane, acetonitrile or toluene. The resulting solution or mixture can be distilled.

Compound of formula (I) can be purified, preferably by distillation, optionally under reduced pressure, or by crystallization.

The condensed crude products from reaction (A) can also be treated with water, optionally water comprising a base, i.e. of alkaline pH, in order to hydrolyze the unreacted compound of formula (II), and compound of formula (I) can be isolated by phase separation and distillation.

Compound of formula (I) may also be purified by dissolution in an aqueous acid, followed by extraction of residual compound of formula (II) and of other, non-basic byproducts with an organic solvent immiscible with water, such as toluene, dichloromethane, or acetic acid esters, followed by basification of the aqueous, acidic phase and extraction or distillation of the compound of formula (I).

Compound of formula (I) may be purified further by conversion into a salt (e.g. a hydrochloride, an acetate, a benzoate, or a formate), recrystallization from a suitable solvent, preferably selected from the group consisting of water, methanol, ethanol, isopropanol, and mixtures thereof, followed by liberation of the unprotonated compound of formula (I) from said salt by treatment with a base.

The method of the present invention can be performed continuously, which provides a more constant product quality than batch wise processes. A continuous process is also more convenient for the large scale production of compounds, because fewer operations and fewer operators are required, because no dangerous accumulation of starting materials occurs, and because the process is easier to control. Alternatively, the method of the present invention can be conducted batch wise.

The method of the present invention uses inexpensive starting materials, does not require the use of expensive hydrides or borane as reducing reagent, can be done at relatively low temperatures and does not require the use of copper chromite. Moreover, the method of the present invention is requires less process steps than the previously disclosed methods resulting in lower production costs for compound of formula (I) and its salts.

EXAMPLES

GC Method column: ZS-G000111, HP-5 ms, 30 m×0.25 mm×0.25 μm initial temperature: 60° C.

initial time: 1.0 min number of ramps: 1 rate: 20 K/min final temperature: 280° C.

GC-MS Method

For the GC part of GC-MS, the same above listed parameter as for GC alone were used.

Example A

Preparation of Compound of Formula (II)

A mixture of 2-cyanocyclopentanone (20.0 g, 183 mmol, prepared as described in Fleming et al., J. Org. Chem. 2007, 72, 1431-1436 in the Supporting Information), water (24.7 ml), and sodium cyanide (14.8 g, 302 mmol) was cooled with an ice bath to a temperature of 5° C. to 10° C. A mixture of sulfuric acid (29.3 ml, 550 mmol) and water (24.7 ml), said mixture having a temperature of 10° C., was added drop wise within 0.5 h while stirring. The ice bath was then removed, and the mixture was stirred for 2.5 h at room temperature. Water (50 ml) was added, and the mixture was extracted with ethyl acetate (3×100 ml). The combined extracts were dried with magnesium sulfate, and pyridine (51 ml, 631 mmol) was added. The solution was cooled with an ice bath to a temperature of 5° C. to 10° C., and acetyl chloride (40.0 ml, 561 mmol) was added drop wise. The resulting mixture was stirred at 0° C. for 2 h, and then at room temperature overnight. After filtration and concentration under reduced pressure, toluene (100 ml) and ethyldiisopropylamine (94 ml, 553 mmol) were added to the residue, and the mixture was stirred at 100° C. for 6 h, and at room temperature overnight. The mixture was poured into a mixture of aqueous, concentrated hydrochloric acid (68 ml) and water (70 ml), phases were separated, the aqueous phase was extracted with ethyl acetate (3×150 ml), the combined extracts were washed with brine, dried with magnesium sulfate, and concentrated under reduced pressure to yield 22.5 g of a dark oil. Distillation (2 mbar) yielded 8.6 g (40%) of compound of formula (II) (bp 66-71° C.).

$^1$H NMR (CDCl$_3$, 400 MHz) compound of formula (II): δ 2.17 (quint, J=7 Hz, 2H), 2.83 (t, J=7 Hz, 4H).

Example B

Preparation of Compound of Formula (II-a)

A mixture of isopropanol (1.0 ml), compound of formula (II) (0.10 g, 0.85 mmol), prepared according to example A, and palladium on charcoal (5%, containing 57% of water; 0.10 g, 0.02 mmol) was placed under hydrogen, and stirred vigorously at 80° C. for 21 h. The mixture was filtered, and the filtrate concentrated under reduced pressure, to yield 0.10 g of compound of formula (II-a).

$^1$H NMR (CDCl$_3$, 400 MHz) compound of formula (II-a): δ 1.82 (m, 1H), 2.05 (m, 1H), 2.17 (m, 4H), 3.14 (m, 2H). Analysis by GC-MS indicated a purity of 73% for compound of formula (II-a).

Compound of formula (II-a) can be used as substrate for the preparation of compound of formula (I) according to example 1, wherein compound of formula (II-a) is used instead of compound of formula (II)

Example 1

A mixture of compound of formula (II) (496 mg, 4.20 mmol), prepared according to example A, THF (110 ml), and Pt on charcoal (0.88 g, 0.45 mmol, 10% by weight Pt based on total weight of catalyst) was placed in an autoclave and stirred under hydrogen (55 bar) at 140° C. for 16 h. The mixture was filtered and concentrated under reduced pressure, to yield 410 mg of an oil. Analysis by GC-MS indicated that 43% of compound of formula (I) had been formed.

Example 2

A mixture of compound of formula (II) (2.04 g, 17.3 mmol), prepared according to example A, THF (110 ml), and Pt on charcoal (1.66 g, 0.85 mmol, 10% by weight Pt) was placed in an autoclave and stirred under hydrogen (55 bar) at 88° C. for 16 h and then at 100° C. for 17 h. The mixture was filtered and concentrated at atmospheric pressure, and the residual oil was distilled to yield 2.6 g of a mixture of THF and compound of formula (I). Analysis by GC-MS indicated a purity of 67% for compound of formula (I).

Example 3

A mixture of compound of formula (II) (497 mg, 4.21 mmol), prepared according to example A, THF (109 ml), and Rh on charcoal (0.87 g, 0.42 mmol, 5% by weight Rh) was placed in an autoclave and stirred under hydrogen (55 bar) at 130° C. for 11 h. The mixture was filtered and concentrated at atmospheric pressure, and the residual oil was analyzed by GC and (CC-MS. Analysis by GC indicated a purity of 73% for compound of formula (I). A sample was purified by extraction and distillation.

$^1$H NMR (CDCl$_3$, 500 MHz) delta 1.23 to 1.33 (m, 2H), 1.45 to 1.65 (m, 2H), 1.68 to 1.77 (m, 2H), 2.47 to 2.55 (m, 4H), 2.99 (m, 2H)

$^{13}$C NMR (CDCl$_3$, 1.25 MHz) delta 26.42, 32.90, 44.45, 54.85.

Example 4

A mixture of compound of formula (II) (494 mg, 4.18 mmol), prepared according to example A, THF (110 ml), and on charcoal (0.89 g, 0.44 mmol, 5% by weight Ru) was placed in an autoclave and stirred under hydrogen (55 bar) at 130° C. for 24 h. The mixture was filtered and concentrated at atmospheric pressure, and the residual oil was analyzed by GC and GC-MS. Analysis by GC indicated a purity of 63% for compound of formula (I).

Example 5

A mixture of compound of formula (II) (3.86 g, 32.7 mmol), prepared according to example A, THF (89 ml), and Rh on alumina (1.35 g, 0.66 mmol, 5% by weight Rh) was placed in an autoclave and stirred under hydrogen (80 bar) at 120° C. for 22 h. The mixture was filtered and concentrated at 250 mbar, and the residual oil (5.44 g) was distilled at 16 mbar. The fraction distilling at 160° C. (1.64 g) was analyzed by GC-MS, which indicated a purity of 40% for compound of formula (I).

Example 6

A mixture of compound of formula (II) (1.10 g, 9.31 mmol), prepared according to example A, THF (90 ml), and Rh on alumina (0.39 g, 0.19 mmol, 5% by weight Rh) was placed in an autoclave and stirred under hydrogen (80 bar) at 120° C. for 22 h. The mixture was filtered and concentrated at 250 mbar, and the residual oil (1.96 g) was distilled at 16 mbar. The fraction distilling at 160° C., (0.63 g) was analyzed by GC-MS, which indicated a purity of 58% for compound of formula (I). This corresponds to a yield of 35% of compound of formula (I).

The invention claimed is:

1. A method for the preparation of a compound of formula (I);

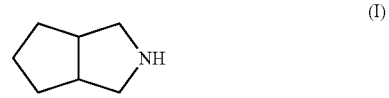

the method comprising a reaction (A), wherein a compound of formula (II) is reacted with a reagent (A-rea) in the presence of a catalyst (A-cat),

wherein the reagent (A-rea) is hydrogen; and
the catalyst (A-cat) is a catalyst conventionally used in hydrogenation reactions of unsaturated organic compounds.

2. The method according to claim 1, wherein the catalyst (A-cat) is selected from the group consisting of a metalcatalyst (A-metcat), a metalcatalyst (A-metcat) on a support (A-sup), and mixtures thereof; wherein
the metalcatalyst (A-metcat) is a substance conventionally used in organic reduction reactions and is derived from Pd(0), Pd (I), Pd(II), Ni(0), Ni(I), Ni(II), Pt(0), Pt(I), Pt(II), Pt(IV), Co(0), Co(II), Ru(0), Ir(0), Rh(0), Rh(I), Rh(III), Cr(III), Cu(0), Cu(I) or Cu(II); and
the support (A-sup) is a support conventionally used for supporting a metalcatalyst, which is used in organic reduction reactions.

3. The method according to claim 1, wherein the catalyst (A-cat) is selected from the group consisting of Raney nickel, Raney cobalt, platinum on carbon, palladium on carbon, ruthenium on carbon, rhodium on alumina, and rhodium on carbon.

4. The method according to claim 1, wherein the reaction (A) is carried out in the presence of an auxiliary substance (A-aux), wherein the auxiliary substance (A-aux) is selected from the group consisting of N(R1)(R2)R3, diazabicyclo [2.2.2]octane, [N(R4)(R5)(R6)R7$^+$][X$^-$], sodium fluoride, potassium fluoride, sodium hydroxide, potassium hydroxide, sodium carbonates, potassium carbonate, sodium hydride, acetic acid, formic acid, and hydrogen chloride; wherein
R1, R2 and R3 are identical or different and independently selected from the group consisting of H and C$_{1-4}$ alkyl;
R4, R5, R6 and R7 are identical or different and independently selected from the group consisting of H and C$_{1-4}$ alkyl; and
X$^-$ is selected from the group consisting of fluoride, chloride, hydroxide, and carbonate.

5. The method according to claim 4, wherein the auxiliary substance (A-aux) is selected from the group consisting of ammonia, trimethylamine, triethylamine, diazabicyclo [2.2.2]octane, tetrabutylammonium fluoride, sodium fluoride, potassium fluoride, sodium hydroxide, potassium hydroxide, sodium carbonates, potassium carbonate, sodium hydride, acetic acid, formic acid, and hydrogen chloride.

6. The method according to claim 1, wherein the reaction (A) is done in a solvent (A-sol), wherein the solvent (A-sol) is selected from the group consisting of water, acetic acid, propionic acid, tetrahydrofuran, 2-methyl-tetrahydrofuran, dioxane, 1,2-dimethoxyethane, methanol, ethanol, 1-propanol, 2-propanol, butanol, pentanol, ethylene glycol, glycerol, and mixtures thereof.

* * * * *